United States Patent [19]
Boivin et al.

[11] Patent Number: 5,955,070
[45] Date of Patent: Sep. 21, 1999

[54] **INOCULATION BY *GEOTRICHUM CANDIDUM* DURING MALTING OF CEREALS OR OTHER PLANTS**

[75] Inventors: Patrick Boivin, Messein; M'Baka Malanda, Nancy, both of France

[73] Assignee: Institut Francais des Boissons de la Brasserie, Vandoeuvre, France

[21] Appl. No.: 08/945,242

[22] PCT Filed: Apr. 23, 1996

[86] PCT No.: PCT/FR96/00621

§ 371 Date: Jan. 26, 1998

§ 102(e) Date: Jan. 26, 1998

[87] PCT Pub. No.: WO96/34085

PCT Pub. Date: Oct. 31, 1996

[30] Foreign Application Priority Data

Apr. 24, 1995 [FR] France .................................. 95 05038

[51] Int. Cl.⁶ ...................................................... C12N 1/20
[52] U.S. Cl. ........................ 424/93.5; 435/254.1; 426/12; 426/16; 426/64
[58] Field of Search ........................ 424/93.5; 435/254.1; 426/12, 16, 64

[56] References Cited

FOREIGN PATENT DOCUMENTS 94 16053   7/1994   WIPO .............................. C12C 1/02

OTHER PUBLICATIONS

Marinchenko, V.A., et al.: "Effect of fungal cellulases on enzymic activity of malt"; Applied Biochemistry and Microbiology, Nov.–Dec. 1979; vol. 15, No. 6, Plenum Publishing Corporation, pp. 670–673.

Douglas, P.E., et al.; "A microbiological evaluation of barley malt production"; Journal of the Institute of Brewing; Mar.–Apr. 1988; vol. 94, pp. 85–88.

Moore–Landecker, Fundamental of the Fungi, 2d ed., 1982, Prentice–Hall, Inc., NJ, p. 432.

*Primary Examiner*—Jean C. Witz
*Attorney, Agent, or Firm*—Venable; Michael A. Gollin

[57] ABSTRACT

The invention provides micro-organism strains of the *Geotrichum candidum* family, obtainable by selecting and cloning natural strains of the micro-organism, and which have the following properties: a lipase activity of less than $2.5 \cdot 10^{-7}$ nKat per cell; a substantially complete inhibition of undesirable flora developing during malting; and a lack of mutagenic activity as measured by the Ames test.

23 Claims, 3 Drawing Sheets

INOCULATION BY *GEOTRICHUM CANDIDUM* DURING MALTING OF CEREALS OR OTHER PLANTS

FIELD OF THE INVENTION

The invention relates to the use of a given micro-organism in the process of malting of cereals or other vegetables, such as wheat, barley, rice, sorghum, maize, buckwheat for the control of the growth of the microflora able to contaminate and colonize these cereals or other plants.

The present invention will find its application in the area of the malting industry and, consequently, with brewers-maltsters but also in the context of distilleries and, generally, in every industry using cereals or malted plants.

BACKGROUND OF THE INVENTION

It should be pointed out that the cereals or other plants, for example, barley, even before undergoing the different operations of treatment and transformation in a malting unit are naturally contaminated with many micro-organisms. Thus, in the particular example of barley, this latter is the natural host of a diverse and considerable flora which is composed, principally, of bacteria and yeasts as well as filamentous fungi. Indeed, this flora contaminates and colonizes the barley grain both in the field as well as during storage. The nature and number of these micro-organisms depend, of course, on the conditions of cultivation and climate, as well as on the duration and conditions of storage.

The various analyses performed on these micro-organisms derived from the fields has enabled about a hundred species to be listed. However, the most frequently encountered moulds are Alternaria, Clasdosporium and Fusarium.

Moreover, it has been observed that in the case of a late harvest or when the harvesting is done in wet weather, the grain exhibits considerable contamination with Fusarium. As for the flora which contaminates and colonizes the grain during storage, thus prior to malting, it is composed of xerophilous filamentous fungi. There again, the study of these filamentous fungi has made it possible to demonstrate that the predominant species are Aspergillus and Penicillium.

Ultimately, the problem resides in the fact that the different operations which consist in transforming the cereals, in particular, into malt, are performed under conditions which promote the growth of the microflora already present on the grain. Actually, during the malting, conditions exist, particularly in respect to moisture, temperature, nutrients or also the residence time in the various vessels, which finally allow the bacteria and yeasts to multiply on a scale ranging from $10^2$ to $10^4$ without taking in account a considerable growth of moulds.

In this connection it is worthwhile recalling the different stages of the malting process. More precisely, after preparation of the grain, the latter undergoes a steeping operation for a period of about forty hours, in order to increase the moisture content by 35 to 45%. Then follows the germination during a period of about six days at a temperature of about 16°. After that, kilning of the malt is performed which consists of drying the grain at different discrete steps of temperature, increasing from about 50° to 80° Celsius. Then follow deculming and the storage of the malt finally obtained.

This uncontrolled growth of the microflora constitutes a drawback as far as it affects the quality of the malt and, of course, of the final product, for example the beer which is obtained from it. Indeed, it is responsible for the production of inhibitors of germination. Moreover, it results in a production of undesirable enzymes such as lipases, oxidases, proteases, etc. Some of these micro-organisms present in an overabundant quantity are also responsible for undesirable flavors. The beer finally obtained may, thus, possess a musty or even earthy or oxidized flavor.

Generally in the brewing area the phenomenon of gushing is dreaded which, as its name indicates, consists in the beer gushing out of the bottle when it is opened, owing to an instability of the carbon dioxide. Indeed, specific micro-organisms are responsible for this. Consequently, it is advisable to avoid their presence or at the very least prevent their quantity from exceeding a given threshold. Now the only way to be sure of achieving this result consists in avoiding substantial growth of the micro flora and hence of the precursors of gushing produced in particular by Fusarium.

To this it may be added that the presence of certain micro-organisms such as the bacteria of the Pediococcus type has consequences on the filtration rate of the mash and leads to a rapid clogging of the filters.

However, the major drawback encountered as a result of the large growth of moulds consists of a large increase in the risk of formation of mycotoxins since toxicogenic moulds are naturally present on cereals and plants.

Indeed, inspite of the drawback previously mentioned, this growth of the microflora is scarcely controlled in the malt houses. The fault responsible for this is the absence of effective means to actually perform this control.

Thus, only a disinfection operation can be conducted at the time of steeping by the addition of hypochlorite or limewater. If the addition of such disinfectants has only a slight effect on the microflora, it presents no less a risk for certain operations of the malting process. In particular in the case where well-defined doses are exceeded, these disinfectants represent a risk for the germination of the grains and may lead to problems of off-taste in the beer for example.

The objective of the present invention is to remedy all of these drawbacks by preventing the growth, more particularly, of the undesirable microflora, through the inoculation of a specific micro-organism which has been selected in the light of the convincing results to which it has led.

It has been suggested to use in a malting process an inoculation of starter culture containing *Geotrichum candidum* to control the growth of the microflora.

The use of lactic acid bacteria which is widespread in the agrifoodstuff processes and even in malt-houses to produce acid malts, has been suggested for the reduction of the growth of fungal flora, in particular of Fusarium (WO 94/16053). However, the inoculation of lactic acid bacteria during malting only permits a partial inhibition of the growth of the fungal flora and does not make possible the inhibition of the mycotoxins during the malting process.

*Geotrichum candidum* which is naturally present on barley during germination and on the finished malt has been suggested, on the one hand, to inhibit the growth of toxicogenic flora during malting and the synthesis of mycotoxins and, on the other, to improve the biochemical and physico-chemical quality of the malt.

*Geotrichum candidum* is very common in the dairy environment. Most of the strains have been isolated from milk and cheese. It forms part of the flora naturally present in the manufacture of cheese from raw milk. In the dairy industry attempts have been made for a long time to prevent the growth of this yeast-like fungus which, poorly controlled, is capable of causing defects in the appearance of the cheese. In recent years we have witnessed on the part of the industrial cheese-makers a revival of interest in *Geotrichum candidum* owing to its role in the improvement of the organoleptic qualities of the cheeses and the inhibition of the growth of pathogenic bacteria and undesirable moulds in the ripening process.

The lipase activity of this micro-organism, in great demand in the cheese industry, was considered as a major drawback in the field of malting, in particular for the organoleptic adverse effects to which it can lead (Drost et al. ASBC Journal, 1990, 124–131; Kobayashi et al. Journal of Fermentation and Bioengineering, 1993, 371–375).

BRIEF SUMMARY OF THE INVENTION

The present invention relates to the use of a microorganism of the *Geotrichum candidum* family in the malting process of cereals or other plants such as wheat, barley, rice, sorghum, maize, buckwheat for the control of the growth of the flora able to contaminate and colonize these cereals or other plants.

Furthermore, according to the invention, strains selected from *Geotrichum candidum* are inoculated during malting, either in the form of a pure culture, or in the form of a mixed culture in combination with one or more other microorganisms, in particular lactic acid bacteria.

According to the invention, the inoculation of *Geotrichum candidum* is done in proportions included between $10^5$ and $10^9$, preferably between $10^7$ and $10^8$ colony forming units (CFU) per kilogram of cereals or other plants; this is done so as to obtain the desired result, namely the control of growth of the microflora.

The advantages obtained as result of this invention consist, essentially, in that the *Geotrichum candidum* has an inhibitory effect on the undesirable flora such as Fusarium, Penicillium, Aspergillus, without taking into account the fact that it makes it possible to inhibit the production of secondary metabolites of the undesirable flora such as the mycotoxins and the precursors of gushing.

The invention also relates to the use of this microorganism in the malting of cereals and other plants, such as wheat, barley, rice, sorghum, maize, buckwheat for the control of the gushing of the beverage obtained from the malt.

It should be pointed out that, in addition, this improvement of the health of the malt is accompanied by qualitative assets since as a result of this inoculation of *Goetrichum candidum* a reduction of the fatty acids of the wort is obtained which, for example, are often responsible for the problem of off-taste of the beer, such as the oxidized FLAVOR and poor head retention. Furthermore, the inhibition by *Geotrichum candidum* of certain flora responsible for the synthesis of polysaccharides leads to an improvement from the point of view of the filtration kinetics.

Finally, as a result of the use of certain strains of *Geotrichum candidum* it is possible to promote the growth of lactic acid bacteria which are capable of reinforcing the inhibitory effect on the undesirable flora and of improving the quality of the malt by a natural lowering of the pH.

The inventors have been able to observe the disparity of the effects of the different strains of *Geotrichum candidum* on the inhibition of the microflora and on the inhibition of the production of secondary metabolites of the undesirable flora: mycotoxins and precursors of gushing as well as on the organoleptic properties or the physico-chemical properties of the beer.

By physico-chemical quality is meant in particular:
the reduction of the fatty acids of the wort which are often responsible for the problems with the off-taste of the beer, such as the oxidized flavor or also poor head retention;
an improved filtration of the mash owing to the inhibition of certain flora responsible for the synthesis of polysaccharides;
the absence of the gushing.

The present invention focuses on the means of selection of the *Geotrichum candidum* strains exhibiting both the inhibitory properties described above and the absence of the drawbacks, essentially of the organoleptic type, resulting from the low lipase activity.

The means or procedures of selection of said strains comprise a selection of the natural strains taken from the malt according to a combination of qualitative and productive criteria, certain of these criteria being essential, others, in combination with the essential criteria, being highly recommended, this selection being made after the isolation and cloning of the natural strains.

The essential criteria are:
a): a low lipase activity,
b): the inhibition of the undesirable flora growing during malting,
c): the production of a strain neither mutagenic nor toxicogenic.

The preferred strains are those which, in addition, exhibit:
d): a stability of the solution of spores for more than 6 months,
e): an abundant production of spores ranging from $10^7$ to $10^8$/ml,
f): an improvement of the mash filtration rate, or a combination of these.

The synthesis of lipase during malting must be as low as possible since this enzyme may lead to problems of the oxidized flavor of the beer. The lipase potential of the *Geotrichum candidum* strains selected for their use in malting must be as low as possible so that there is no exogenous lipase synthesis during the malting process.

The present invention also focuses on the *Geotrichum candidum* strains capable of being obtained by the selection process such as that described above and comprising at least the criteria a), b), c) and preferably in combination with the aforementioned, the criteria e), f) or g) or a combination of the latter.

The strains capable of thus being obtained preferably have a lipase activity less than $2.5 \times 10^{-7}$ nKat/cell (nmole/sec/cell), lead to total inhibition of the undesirable flora and do not possess mutagenic potential.

In addition, the production of spores must attain preferably $10^7$ spores/ml, and even more preferably be located between $10^7$ and $10^8$ per ml.

The selection process has made it possible to select *Geotrichum candidum* strains which provide materially very good results whether from the point of view of the inhibition of the undesirable flora or of the improvement of the quality of the malt which proves moreover to be significant and results in an improved filtration of the mash and a higher yield of extract. Strains such as those obtained by this process were deposited under the terms of the Budapest Treaty on Sep. 6, 1994 with the Collection Nationale de Culture de Micro-organismes at the Pasteur Institute and were registered under the No. I-1475 and No.I-1474. Tests which consisted of inoculating one of these *Geotrichum candidum* strains in proportions included between $10^7$ and $10^8$ (CFJ) per kilogram of barley, and performed as early as the first wet steeping in the case of the malting of "six row winter" barley, corresponding therefore to a barley of average quality, have made it possible to demonstrate that it is possible to obtain, ultimately, a malt of very good quality.

Throughout the text and in particular in the examples the strain I-1474 is the strain GC3; the strain I-1475 is the strain GC4.

It is surprising to discover that these advantages resulting from the invention are obtained without consequence either for the manufacturing process of the beer or for the beer which is produced by it. More precisely, no significant variation of the process has been observed. Furthermore, the beer obtained from the malt treated with *Geotrichum candidum* is similar from an organoleptic point of view to the beer derived from untreated malt. The aromatic profile is identical and in triangular tasting there is scarcely any difference.

Other objectives and advantages of the present invention will become apparent during the description which follows explaining the methods for inoculating *Geotrichum candidum*.

BRIEF DESCRIPTION OF THE DRAWINGS

The understanding of this description will be facilitated by reference to the drawing enclosed in the appendix and in which.

DETAILED DESCRIPTION OF THE INVENTION

The objective of the present invention is to interfere in the malting process for the purpose of improving the health and quality of the malt finally obtained from cereals or other plants, such as wheat, barley, rice, sorghum, maize, buckwheat.

The present description will be more particularly concerned with the transformation of barley into malt but it is obvious that the present invention is in no way limited to such an application and that it applies to all cereals or plants capable of undergoing a malting process (plant material capable of undergoing malting).

Figure 1:
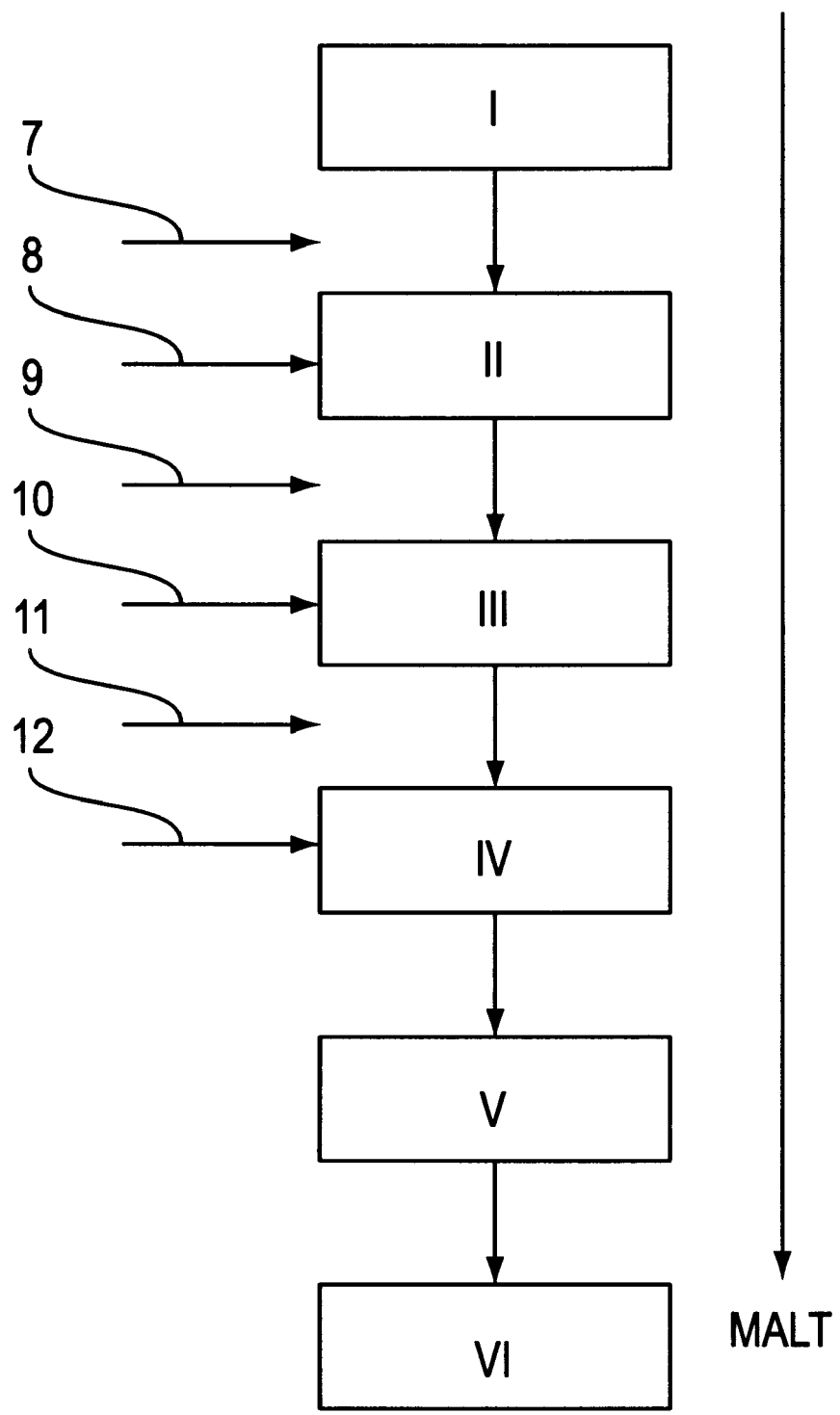
FIG. 1 shows the main steps of the malting process; in addition arrows represent the stages during which it is possible to carry out an inoculation of selected microorganisms.

FIG. 1 illustrates schematically the six stages I, II, III, IV, V, VI which define this malting process. Thus, after preparation of the grain corresponding to the first stage I, the barley undergoes a steeping operation which consists of immersing the barley in water in order to increase its moisture content to 35 to 45%. It should be noted that during this steeping operation the water is changed one or more times in order to ensure a washing and oxygenation action on the grain.

After this second stage II, the barley thus humidified, passes to stage III which is that of germination. Kilning follows (stage IV) which consists of drying the grain by subjecting it to discrete temperature steps between 50° Celsius and 80° Celsius and by respecting at each step the defined drying time.

This is followed by stage V which consists of deculming. The malt which is produced is then stored, which constitutes the last step VI of this malting process.

It is easy to understand that the supply of moisture, the residence times and the temperatures to which the cereals or other plants are subjected during these different steps of malting constitute conditions favourable for the growth of the microflora already present prior to malting.

The aim of the present invention is to prevent the growth of the undesirable microflora in particular by the inoculation of a micro-organism particularly well adapted for this purpose. Indeed, the micro-organism, which in the context of the application concerned shows the desired results, is derived from the *Geotrichum candidum* family.

In this regard, the times during the malting process when this inoculation can take place are marked by arrows 7 to 12 in FIG. 1.

Thus, *Geotrichum candidum* may be inoculated and homogenized by aeration in the first steeping water before the introduction of the barley into the vessel. The inoculation may be carried out by spraying directly on the barley arriving in the steeping vessel. However, it may be preferred to carry out this inoculation during this first wet steeping but even during two or three wet steeping, especially if the barley is highly contaminated.

This inoculation can also be performed during the transport of the barley between the steeping vessel to the germination vessel and at this stage of the process to spray water or germination activators on the barley grain. It should be noted that that does not raise any problems because provision is usually made in the malting units and at this stage of the process to spray germination activators on the barley grain.

Finally, and as represented in FIG. 1, this inoculation can be performed also during germination, during the transfer towards the kilning or even at the time of drying the grain.

EXAMPLE I

Selection process for the *Geotrichum candidum* strains.

Table I presents the lipase activity in nanomoles per second per cell of different strains of *Geotrichum candidum* after an incubation for a week at 20° C. in a malt extract medium. The strains L+ and L− are *Geotrichum candidum* isolated from dairies and cheese factories representing the extremes of lipase potential. The other strains were isolated from the malting process. It is observed that the "malting" strains have a low lipase potential, lower than the "dairy" strains. This test in liquid medium makes it possible to select the *Geotrichum candidum* strains with low lipase potential.

TABLE I

| Strains | L+ | L− | GC1 | GC2 | GC3 |
|---|---|---|---|---|---|
| Lipase activity ($10^{-7}$ nmole/sec/cell) | 6.4 | 2.5 | 0.3 | 1.7 | 1.5 |

The aim of the second test is to show the effect of different strains selected on the total lipase activity in the grain expressed in nanomoles per second and per gram of dry matter during malting depending on whether *Geotrichum candidum* has been inoculated or not.

The results of this test are expressed in the following Table II.

TABLE II

| Strains | Control | GC1 | GC2 | GC3 | GC4 | GC5 |
|---|---|---|---|---|---|---|
| Lipase activity on green malt nmole/sec/gram. | 19.9 | 15.1 | 16.9 | 14.8 | 11.0 | 11.0 |

This test shows a variation in the total lipase activity on green malt, resulting from the activity of barley and from the growth of the microflora. The difference between the test with and without inoculation of various strains results on the one hand from the synthesis of lipase by *Geotrichum candidum*, the number of cells present on the green malt and the inhibition of a flora with lipase potential by *Geotrichum candidum*. It is observed that the strains tested in this example lead to a lower lipase activity on the green malt than the control. This test makes it possible to select the *Geotrichum candidum* strains leading to a low lipase activity on green malt.

The uncontrolled growth of certain flora during malting may lead to a variation in the speed of the mash filtration, an important qualitative factor in the expectations of the brewer. The decrease of the speed of the filtration may be due to the synthesis of polysaccharides, the improvement due either to the synthesis of cellulolytic enzymes ($\beta$-glucanases and pentosanases) or to the inhibition of the flora responsible for the synthesis of polysaccharides. As *Geotrichum candidum* may have different actions, we have used for the selection of strains meeting the expectations of the brewer, a test making it possible to quantify the speed of the filtration of the malt, designated "TEPRAL filtration". Table III gives the kinetic values for the filtration and sparging of the mash of different malts obtained with or without inoculation with *Geotrichum candidum* during malting. GC1, GC2, GC3 and GC5 are the different strains of *Geotrichum candidum* tested.

TABLE III

| Strain | Uninoculated control | GC1 | GC2 | GC3 | GC5 |
|---|---|---|---|---|---|
| Filtration kinetics (gram/min) | 23.2 | 27.6 | 28.8 | 40 | 8.8 |
| Sparging kinetics (gram/min) | 42 | 42.8 | 40 | 56.4 | 10.4 |

As shown in Table III, the speed of mash filtration depends on the strain of *Geotrichum candidum* used. The strains which delay the filtration of the mash should be discarded.

The productivity of *Geotrichum candidum* as well as their stability with time is an important economic parameter for strain selection. Tests of productivity in a fermenter and of stability at 4° C. have been developed. Table IV indicates the values of productivity and stability of different *Geotrichum candidum* strains.

TABLE IV

| Strain | GC1 | GC2 | GC3 | GC4 | GC5 |
|---|---|---|---|---|---|
| Productivity:number of spores per ml ($\times 10^6$) | 20 | 100 | 50 | 90 | 22 |
| % viable spores after 8 weeks storage at 4° C. | 80% | 8% | 50% | 90% | 100% |

The *Geotrichum candidum* strains have variable productivity and stability.

The inhibition of the undesirable flora growing during malting is verified for the different strains tested.

These tests are supplemented by a test of the toxicology and mutagenicity of the strains.

These different tests have made it possible to select *Geotrichum candidum* strains which give materially very good results whether from the point of view of inhibition of the undesirable flora or of the improvement of the quality of the malt which proves moreover to be significant and results in a lower lipase activity and improved filtration of the mash.

EXAMPLE II

Effect of the inoculation with *Geotrichum candidum* on the growth of the microflora:

The advantage of carrying out an early inoculation consists in the fact that the growth of the microflora is controlled right from the start.

Experiments have demonstrated that an inoculation in amounts of about $10^5$ to $10^9$, and preferably between $10^7$ and $10^8$ colony forming units (CFU) per kilogram of cereals or other plants allows convincing results to be obtained. In this connection, this inoculation may be carried out once or several times during the stages previously mentioned. Furthermore, *Geotrichum candidum* may be inoculated in the form of a pure culture or in the form of a mixed culture, i.e. in combination with other micro-organisms such as lactic acid bacteria. Finally, an alternating inoculation of a pure *Geotrichum candidum* culture or mixed culture, followed by a culture other than *Geotrichum candidum* also constitutes a possible solution.

It is advisable to note in this connection that a mixed or alternate inoculation makes it possible to improve other properties, while maintaining the safety of the malt by a strict control of the growth of the micro-organisms. Thus, that may result in the form of an improvement in the yield of extract or also of the inhibition of undesirable enzymes such as the oxidases or, conversely, the production of useful enzymes, such as the cellulases. Attempts may also be made to modify the flavor of the malt by combining with *Geotrichum candidum* a specific micro-organism or carrying out an alternating inoculation with *Geotrichum candidum* and a specific micro-organism in order to produce the desired result.

Table V below illustrates the advantages resulting from the present invention:

TABLE V

| Moulds | Fusarium-infected barley | "Control" malt | "Geotrichum" malt |
|---|---|---|---|
|  | % OF CONTAMINATED GRAINS | | |
| ALTERNARIA | 20 | 5 | 0 |
| ASPERGILLUS | 20 | 15 | 0 |
| FUSARIUM | 100 | 40 | 5 |

TABLE V-continued

| Moulds | Fusarium-infected barley | "Control" malt | "Geotrichum" malt |
|---|---|---|---|
| | % OF CONTAMINATED GRAINS | | |
| PENICILLIUM | 30 | 10 | 5 |
| GEOTRICHUM | 0 | 0 | 100 |

Thus, Table V shows the percentages of grain contaminated by the moulds most frequently encountered in this field, namely Alternaria, Aspergillus, Fusarium, Penicillium and Geotrichum, depending on whether the measures were taken on barley infected with Fusarium, on control malt, i.e. not subjected to any inoculation and, finally, on Geotrichum malt, i.e. malt obtained from the malting process during which inoculation with *Geotrichum candidum* was performed. The results are, of course, dramatic and revealing to the extent that in the "Geotrichum" malt only 5% of the grain are contaminated by Fusarium and Penicillium, since these figures should be compared with the control malt in which 40% of the grain were found to be contaminated by Fusarium and about 10% by Penicillium.

EXAMPLE III

Effect of *Geotrichum candidum* on the production of mycotoxins during malting:

The object of the table VI below is to show the inhibitory effect of *Geotrichum candidum* on the production of mycotoxins during malting. More precisely, this demonstration is made by means of the assay of zeralenone on barley infected with Fusarium, control malt, i.e. not subjected to any treatment and finally Geotrichum malt.

TABLE VI

| | Fusarium-infected barley | Control malt | "Geotrichum" malt |
|---|---|---|---|
| Zeralenone μg/kg | 3 | 100 | 3 |

EXAMPLE IV

Effect of inoculation with Geotrichum on lipase activity

Figure 2:
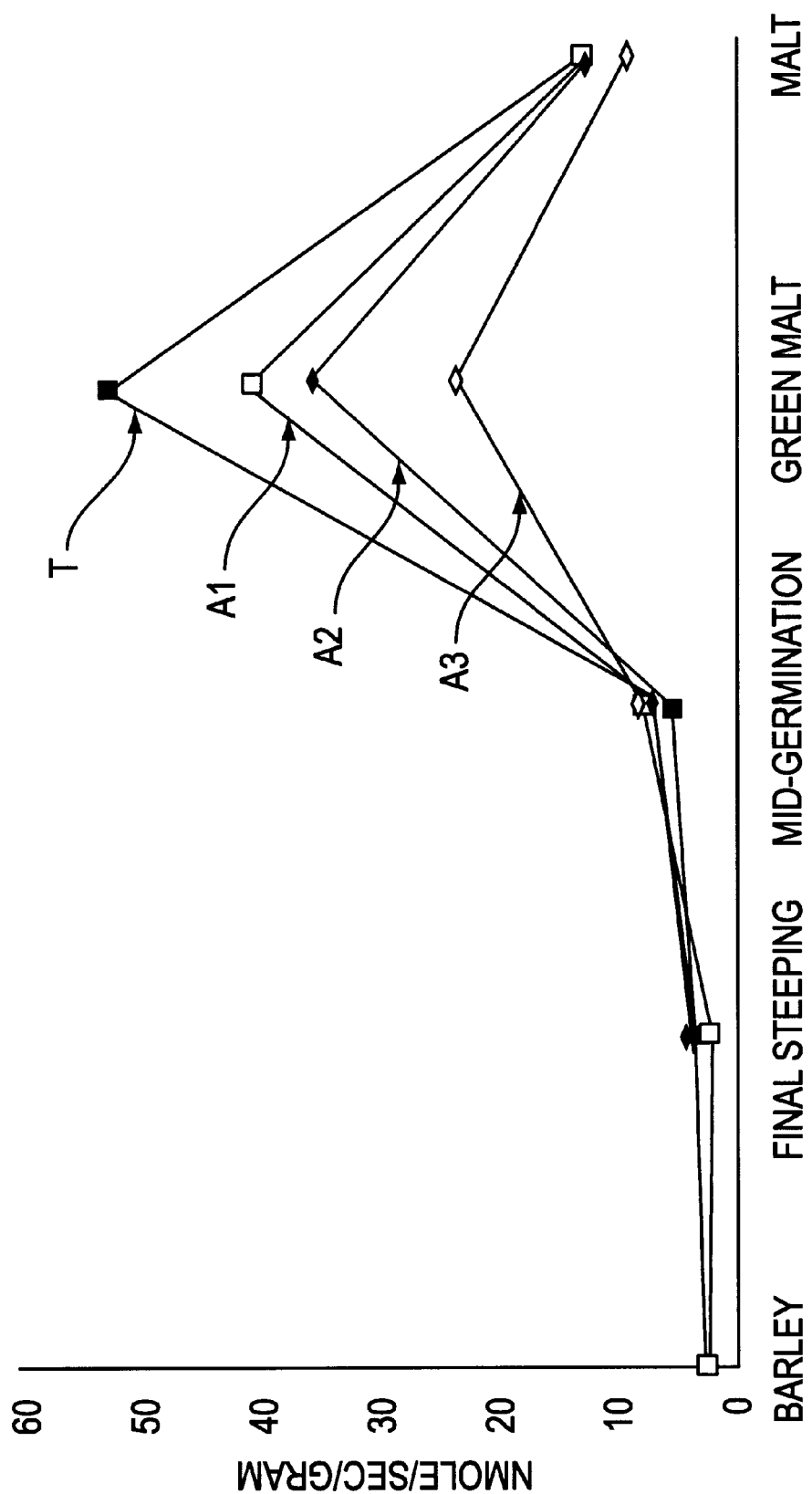
FIG. 2 shows the change in lipase activity during malting depending on whether or not there has been controlled inoculation with *Geotrichum candidum*.

The advantages resulting from the invention also appear in the form of the diagram illustrated in FIG. 2 showing the change in lipase activity during malting depending on whether *Geotrichum candidum* is inoculated or not. In this diagram the stages of the malting process are shown on the abscissa whereas the total lipase activity in the grain in nanomoles per second per gram of dry matter is plotted along the ordinate. Thus, a difference is observed in particular at the green malt stage between the curve T corresponding to the control, i.e. untreated, malt and the curves A1, A2 and A3 corresponding to situations in which various strains of *Geotrichum candidum* designated A1, A2 and A3 are inoculated.

Thus, it is clear that the inoculation of selected strains of *Geotrichum candidum* really enables the growth of the microflora to be controlled and that desired sanitary improvements are indeed obtained, namely:

inhibition of the undesirable flora : Fusarium, Penicillium, Aspergillus, . . . ;

inhibition of the production of secondary metabolites of the undesiarable flora: mycotoxins and precursor of gushing;

enhanced growth of the lactic acid bacteria which may reinforce the inhibitory effect of the undesirable flora and improve the quality of the malt by natural lowering of the pH.

Indeed, the results obtained from the invention are all the more useful because this sanitary improvement is accompanied by major qualitative gains such as:

the reduction of the fatty acids of the wort which are often the cause of the problems with the off-flavor of the beer, such as the oxidized flavor or also poor head retention;

improved filtration of the mash owing to the inhibition of certain flora responsible for the synthesis of polysaccharides.

EXAMPLE V

Figure 3:
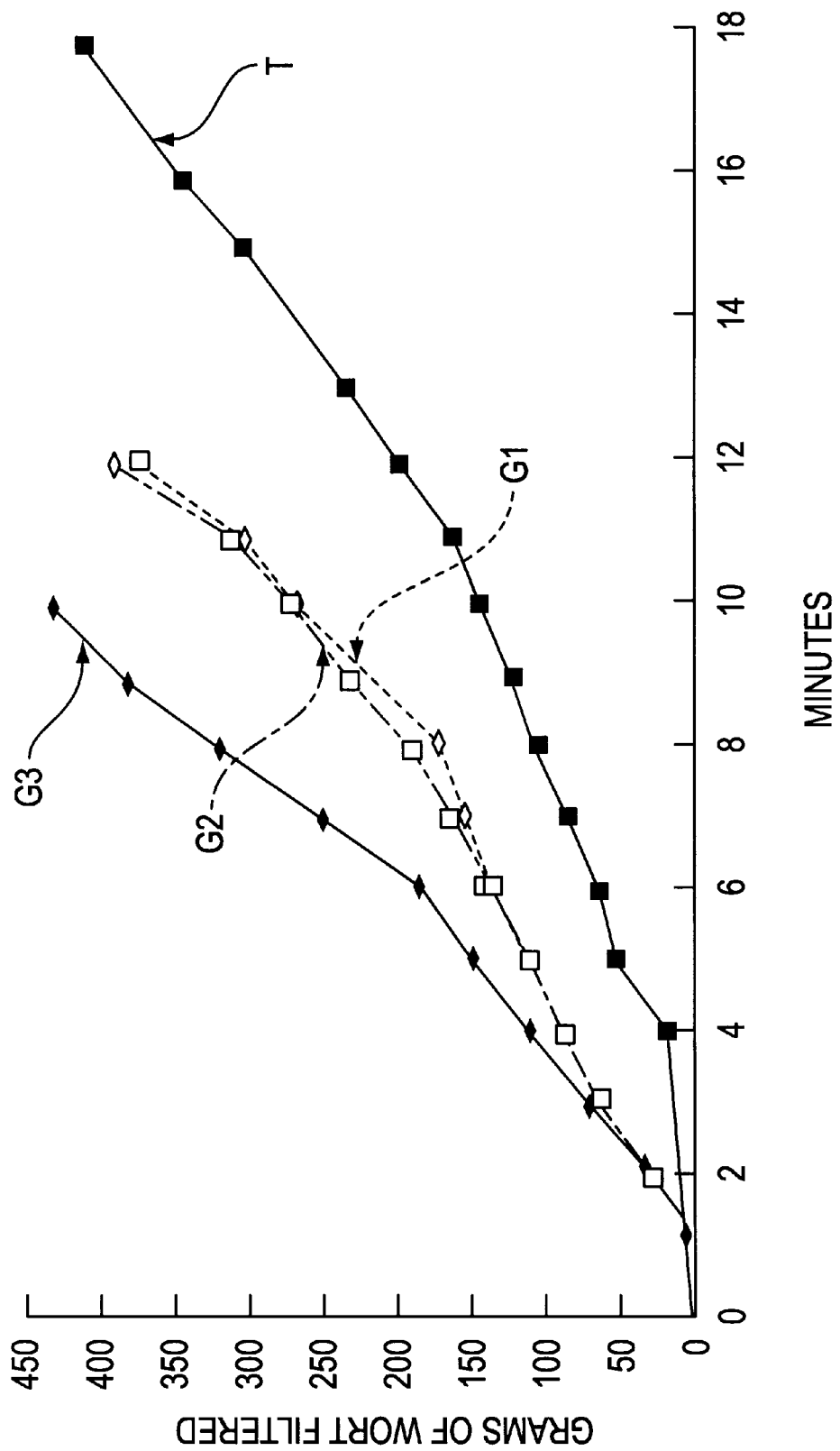
FIG. 3 is a diagram illustrating the kinematics of filtration depending on whether or not there has been controlled inoculation with *Geotrichum candidum*.

Effect of inoculation with *Geotrichum candidum* on the filtration of the mash:

The improvement obtained from the point of view of filtration is illustrated on the diagram in FIG. 3 which shows the filtration kinetics determined according to the method designated "BRASSIN TEPRAL". Thus, in this diagram the time in minutes is given on the abscissa whereas the quantity of wort filtered in grams is shown along the ordinate. The curve T, corresponding to the control malt not subjected to any treatment is situated considerably below the curves GC1, GC2 and GC3 corresponding to malts which have been inoculated with different strains of *Geotrichum candidum* GC1, GC2 and GC3.

EXAMPLE VI

Effect of the inoculation with *Geotrichum candidum* on the quality of the effluents:

It has been possible to observe that the inoculation with *Geotrichum candidum*, quite particularly during the steeping stage corresponding to the malting process, also had beneficial consequences for the effluents. In fact, the analysis of the waters discarded after steeping shows that the inoculation of *Geotrichum candidum* leads to a diminution of the chemical oxygen demand "COD".

Table VII below illustrates, quite particularly, the results obtained following inoculation with *Geotrichum candidum* corresponding to the strain I-1475 in proportions of about $10^7$ (CFU) per kilogram of barley, the malted barley being of the "two row spring" type.

The malting process used was the standard type, i.e. the steeping diagram which was complied with was the following:

1st 5 hours wet steeping followed by 7 hours under air,
2nd 5 hours wet steeping followed by 7 hours under air,
3rd 5 hours wet steeping followed by 7 hours under air.

TABLE VII

| Analyses of steeping water | | |
|---|---|---|
| | COD (mg $O_2$/liter) | |
| | Control | I - 1475 |
| 1st Wet steeping | 969 | 633 |
| 2nd Wet steeping | 691 | 614 |
| 3rd Wet steeping | 883 | 336 |

It is obvious from this table that the results obtained are significant compared with the controls corresponding to malted barley without inoculation with *Geotrichum candidum*.

Consequently, the application of *Geotrichum candidum* to malting in conformity with the invention leads to net progress in the field under consideration.

Although the invention has been described in respect to a particular embodiment, it is well understood that it is in no way limited to it and that it is possible to bring about various modification of forms, materials and combinations of these various elements without departing from the scope and spirit of the invention.

EXAMPLE VII

Toxicity of *Geotrichum candidum* in the Ames test and on the chicken embryo:

Two fungal isolates listed GC3 and GC4 were studied.

Experimental protocol:

Preparation of culture extracts: The two isolates GC93133 and GC93201 were cultured in liquid semi-synthetic medium (Czapek type) containing glucose (procedure of P. Lafont and J. Lafent, Ann. Inst. Pasteur, 1970, 118, 340–348) and, in parallel, in the same liquid medium containing gelose. After incubation (6 days at $-25°$ C.), the cultures in liquid medium were extracted in toto (mycelium and underlying liquid) with refluxing chloroform (3 times successively with 1 vol. of chloroform). After separation, the three chloroform phases were mixed, filtered through Whatman filter paper, dehydrated and evaporated to dryness under nitrogen. Lipids were removed from the residue remaining after evaporation by washing with petroleum ether (extract A). The aqueous phase was concentrated after filtration in a vacuum at a temperature below $45°$ C. (extract B).

The mycelium developed in the medium containing gelose was ground in a 5% aqueous acidified ($H_2SO_4$, 20 ml/L) solution of KCl (wt:v); 1 vol. of this ground mass was diluted with 7 vol. of acetonitrile; after being left to stand for 18 hours at $4°$ C., the suspension was filtered, freed of lipid by washings with petroleum ether and subjected to two successive extractions with chloroform at room temperature. The chloroform phase was evaporated to dryness under nitrogen (extract C).

Toxicity assays on the chick embryo:

A homogeneous batch of eggs (laid the same day in the same incubator) was used for the assays. The test products were inoculated according to the methodology described by P. Lafont and J. Lafont (Bull. Acad. Vet. Fr., 1979, 52, 119–124). The incubation of the eggs was continued until hatching, the development of the embryon being observed by weekly inspecting.

In the case of extracts A and C, the inoculum was prepared aseptically in ethyl alcohol/water (50/50, v/v); in the case of extract B, the concentrate of the aqueous phase was sterilized by filtration through a Millipore G membrane.

Genotoxicity test on bacteria (Ames test):

The heterotrophic strains of *Salmonella typhimurium* catalogued as TA1535, TA1538, TA98 and TA10 were used. The methodology applied was that described by B. N. Ames, J. McCann and E. Yamasaki (Mut. Res., 1975, 31, 347–364) both with respect to bacteriological techniques and the isolation of microsomal preparations from rat liver (animals treated with phenobarbital).

The extracts A and C were incorporated in the superficial layer of the media containing gelose in the form of aseptically prepared dimethylsulfoxide solutions; the B extracts were sterilized by filtration prior to their incorporation.

"Positive" controls were obtained by using as genotoxic agents aflatoxin $B_1$ and 3,4-benzopyrene.

Results:

Toxicity on the chicken embryo:

For each egg the inoculum corresponded to 15 mg (dry weight) of mycelium in the case of the extracts A and C and to 1 ml of culture in the case of the extract B.

The hatching percentage for the different batches of eggs is reported in Table VIII. No significant difference was observed between the control batch and those which had received the culture extracts, nor between the two isolates.

TABLE VIII

| Hatching percentage (%) | | | |
| --- | --- | --- | --- |
| | Extract A | Extract B | Extract C |
| GC 93133 (*) | 95 | 100 | 90 |
| GC 93201 (**) | 90 | 90 | 95 |
| Uninoculated controls (**) | | | 92.5 |
| Inoculated controls - solvents of the extracts A and C (*) | | | 95 |
| Inoculated controls - distilled water (*) | | | 90 |

(*) lot of 20 eggs
(**) lot of 40 eggs

In none of the chickens was any malformation observed.

Ames test:

Two successive assays were carried out using the following concentrations of extract (referred to the dry weight of the mycelium or to the volume of culture) per ml of gelose-containing medium in which the bacterial test strains were cultured:

extracts A and C: 20 and 200 mg extract B: 1 and 10 ml

Under these experimental conditions the extracts of the two *Geotrichum candidum* isolates did not show any effect on the reversion frequency in the strains of *Salmonella typhinurium*, whereas, depending on the strain, the number of revertant colonies per Petri dish were included between 49 (+12) and 195 (+24) in the case of aflatoxin $B_1$ at a concentration of 1 $\mu$l/ml, between 28 (+10) and 218 (+41) in that of 3,4-benzopyrene at a concentration of 0.2 $\mu$g/ml.

Furthermore, control operations have shown that the culture extracts of the two *Geotrichum candidum* isolates did not have an antibiotic effect towards the Salmonella strains.

We may conclude that the assays reported above indicate the absence of the in vitro production of substances toxic and teratogenic for a vertebrate and substances exhibiting genotoxic activities in the case of the two isolates GC3 and GC4.

We claim:

1. An isolated strain of *Geotrichum candidum* which inhibits growth of undesirable flora during malting and which is one of the strains deposited with the CNCM under the numbers I-1474 and I-1475.

2. An isolated strain of *Geotrichum candidum* which inhibits approximately all growth of undesirable flora during malting, and which exhibits lipase activity less than 2.5× $10^{-7}$ nmole/sec/cell and an absence of toxicity or mutagenic activity.

3. An isolated strain of *Geotrichum candidum* according to claim 2, which further exhibits at least one of the following characteristics:

(a) its spores are stable in solution for a period greater than 6 months;

(b) it produces more than $10^7$ spores per ml;

(c) it reduces the chemical oxygen demand during malting;

(d) it enhances growth of lactic acid bacteria during malting;

(e) it inhibits production of mycotoxins during malting;

(f) it improves the rate of mash filtration.

4. A process for malting grain of a plant capable of undergoing malting comprising (I) preparing the grain, (II) steeping the grain, (III) germinating the grain, (IV) kilning, (V) deculming, and (VI) storing the malt produced by the previous stages, which process also comprises inoculation with a strain of *Geotrichum candidum* strain according to claim 2 in quantities ranging from $10^5$ to $10^9$ colony forming units (CFU) per kilogram of said cereal.

5. A malting process according to claim 4, wherein the plant is selected from the group consisting of wheat, barley, rice, sorghum, maize, and buckwheat.

6. A malting process according to claim 4, wherein the inoculation is carried out with $10^7$ to $10^8$ CFU of the *Geotrichum candidum* strain per kilogram of said grain.

7. A malting process according to claim 4, wherein the inoculation with the *Geotrichum candidum* strain is carried out at least once during at least one of the following stages: preparation of the grain, during the first wet steeping, the last wet steeping, intermediate wet steepings, at the time of transfer between the steeping stage and the germination stage, during germination, at the time of transfer between the germination stage and the kilning stage, or during kilning.

8. A malting process according to claim 4 wherein the inoculation is carried out with one of the strains deposited with the CNCM under the numbers I-1474 and I-1475.

9. A method for inhibiting the growth of flora able to contaminate and colonize plant material capable of undergoing malting during the malting of said plant material, the method comprising inoculating said plant material with an inoculant comprising *Geotrichum candidum*.

10. The method of claim 9 wherein the plant material is from a plant selected from the group consisting of wheat, barley, rice, sorghum, maize, and buckwheat.

11. The method of claim 9 wherein the inoculant comprises one or more selected strains of *Geotrichum candidum* in quantities ranging from $10^5$ to $10^9$ CFU per kilogram of said plant material.

12. The method of claim 9 wherein the inoculant comprises one of the *Geotrichum candidum* strains deposited with the CNCM under the numbers I-1474 and I-1475.

13. The method of claim 9 wherein the inoculant comprises a strain of *Geotrichum candidum* which inhibits approximately all growth of undesirable flora during malting, and which exhibits lipase activity less than $2.5 \times 10^{-7}$ nmole/sec/cell and an absence of toxicity or mutagenic activity.

14. The method of claim 13 wherein the strain of *Geotrichum candidum* further exhibits at least one of the following characteristics:

(a) its spores are stable in solution for a period greater than 6 months;

(b) it produces more than $10^7$ spores per ml;

(c) it reduces the chemical oxygen demand during malting;

(d) it enhances growth of lactic acid bacteria during malting;

(e) it inhibits production of mycotoxins during malting;

(f) it improves the rate of mash filtration.

15. The method of claim 9 wherein the inoculant comprises a pure culture of *Geotrichum candidum*, or a mixed culture comprising *Geotrichum candidum* in combination with lactic acid bacteria or one or more other microorganisms.

16. The method of claim 15 comprising inoculating with an inoculant comprising *Geotrichum candidum* in alternation with an inoculant comprising lactic acid bacteria or one or more other microorganisms and lacking *Geotrichum candidum*.

17. The method of claim 9 wherein the inoculating step results in inhibiting gushing of a beverage produced by a process comprising the malting of said plant material.

18. The method of claim 17 wherein the inoculant comprises one or more selected strains of *Geotrichum candidum*.

19. The method of claim 18 comprising inoculating with a strain of *Geotrichum candidum* which inhibits approximately all growth of undesirable flora during malting, and which exhibits lipase activity less than $2.5 \times 10^{-7}$ nmole/sec/cell and an absence of toxicity or mutagenic activity.

20. The method of claim 19 wherein the inoculating strain of *Geotrichum candidum* further exhibits at least one of the following characteristics:

(a) its spores are stable in solution for a period greater than 6 months;

(b) it produces more than $10^7$ spores per ml;

(c) it reduces the chemical oxygen demand during malting;

(d) it enhances growth of lactic acid bacteria during malting;

(e) it inhibits production of mycotoxins during malting;

(f) it improves the rate of mash filtration.

21. A method for identifying an isolated strain of *Geotrichum candidum* which inhibits growth of undesirable microflora during malting, comprising:

(a) obtaining strains of *G. candidum* to be screened;

(b) incubating each strain in malt extract medium, assaying lipase activity, and identifying strains with low lipase potential;

(c) inoculating grain of a plant during malting separately with each strain of *G. candidum* and identifying strains that inhibit growth of undesirable flora during malting;

(d) assaying each strain for toxicity and mutagenicity to growing cells; and (e) identifying a strain which inhibits growth of undesirable flora during malting, and which exhibits lipase activity less than $2.5 \times 10^{-7}$ nmole/sec/cell and an absence of toxicity or mutagenic activity.

22. The method of claim 21, further comprising at least one of the following:

(i) assaying viability of spores of each strain that have been stored for at least six months, and identifying a strain that produces spores that are stable for a period greater than 6 months;

(ii) quantifying spore production by each strain and identifying a strain that produces more than $10^7$ spores per ml;

(iii) inoculating grain of a plant during malting with each strain, assaying mycotoxin production during malting, and identifying a strain that inhibits production of mycotoxins during malting;

(iv) inoculating grain of a plant during malting with each strain, measuring the rate of filtration of the malt, and identifying a strain that improves the rate of mash filtration.

23. An isolated strain of *G. candidum* obtained by the process of claim 21.

* * * * *